(12) United States Patent
Beal et al.

(10) Patent No.: US 6,265,442 B1
(45) Date of Patent: Jul. 24, 2001

(54) TREATMENT OF NEUROLOGICAL DISEASES BY INCREASING BRAIN CONCENTRATIONS OF KYNURENIC ACID

(75) Inventors: M. Flint Beal, Boston; Kenton J. Swartz, Somerville, both of MA (US); Matthew J. During, Rowayton, CT (US); Andrew Freese, Haverford, PA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/034,094

(22) Filed: Mar. 22, 1993

Related U.S. Application Data (63) Continuation of application No. 07/944,679, filed on Sep. 14, 1992, now abandoned, which is a continuation of application No. 07/850,096, filed on Mar. 12, 1992, now abandoned, which is a continuation of application No. 07/758,743, filed on Sep. 12, 1991, now abandoned, which is a continuation of application No. 07/667,966, filed on Mar. 12, 1991, now abandoned, which is a continuation of application No. 07/582,429, filed on Sep. 13, 1990, now abandoned.

(51) Int. Cl.[7] ............................ A61K 31/19; A61K 31/47
(52) U.S. Cl. ............................................. 514/568; 514/312
(58) Field of Search ....................................... 514/568, 312

(56) References Cited

PUBLICATIONS

Gal, E.M., and Shurman, A.D. "Synthesis and Metabolism of L–Kynurenine in Rat Brain," *J. Neurochem.*, 30:607–613 (1978).

Simon, P., et al., "Inhibition of Excitatory Neurotransmission with Kynurenate Reduces Brain Edema in Neonatal Anoxia," *Neuroscience Letters*, 71:361–364, (1986).

Speciale C., et al., "High–Affinity Uptake of L–Kynurenine by a Na+–Independent Transporter of Neutral Amino Acids in Astrocytes," *J. of Neurosci.*, 9(6):2066–2072, (1989).

Beal M.F., et al., "Systemic Approaches to Modifying Quinolinic Acid Striatal Lesions in Rats," *J. of Neurosci.*, 8(10):3901–3908, (1988).

During, M.J., et al., "Potential Neurotoxicity of Tryptophan: Striatal Quinolinic Acid Monitored by Microdialysis," *Society for Neuroscience Abstracts*, 14(1) (1988) (Abstract No. 290.14).

During, M.J., et al., "Quinolinic Acid Concentrations in Striatal Extracellular Fluid Reach Potentially Neurotoxic Levels Following Systemic L–Tryptophan Loading," *Brain Research*, 476:384–387, (1989).

Okuno, E., et al., "α–Ketoglutarate and Pyruvate as Co–Factors of Kynurenine Transaminase in Rat Brain," *Society for Neuroscience Abstracts*, 15 (1989) (Abstract 328.9).

Freese, A., "Excitotoxic Models of Huntington's Disease", *Proc. 1988 HST Forum*, Harvard Univ–MIT Div of Health Sci and Tech, pp. 53–59 (Oct. 28, 1988).

Beal, M.F., et al., "Replication of the Neurochemical Characteristics of Huntington's Disease by Quinolinic Acid," *Nature* 321 (6066):168–171 (1986).

During, M.J., et al., "Indolic and Kynurenine Pathway Metabolites of Tryptophan in Rat Bran: Effect of Precursor Availability on In Vivo Release," *Int'l. Study Group for Tryptophan Research*, Baltimore, (May 9–12, 1989).

During, M.J. and Freese, A., "Branched–Chain Amino Acids in Amyotrophic Lateral Sclerosis," (Letter to Editor), *The Lancet*, II (8612):680 (1988).

During M.J., et al., "Neuroactive Metabolites of L–Tryptophan, Serotonin and Quinolinic Acid, in Striatal Extracellular Fluid," *Federation of European Biochem. Societies Letters*, 247(2):438–444 (1989).

Beal, M.F., et al., "Kynurenine Pathway Measurements in Huntington's Disease Striatum: Evidence for Reduced Formation of Kynurenic Acid," *J. of Neurochem.*, 55(4):1327–1339 (1990).

Swartz, K.J., et al., "Measurement of Kynurenic Acid in Mammalian Brain Extracts and Cerebrospinal Fluid by High–Performance Liquid Chromatography with Fluorometric and Coulometric Electrode Array Detection," *Analytical Biochem.*, 185:363–376 (1990).

Freese, A., et al., "Regional Brain Quinolinic Acid Levels and Neurochemical Markers of Toxicity: Effects of Acute vs. Chronic Tryptophan Feeding," *Society for Neuroscience Abstracts*, 15 (1989) (Abstract No. 306.3).

Moroni, F., et al., "Presence of Kynurenic Acid in the Mammalian Brain," *J. Neurochem.*, 51(1):177–179, (1988).

Foster A.C., et al., "Kynurenic Acid Blocks Neurotoxicity and Seizures Induced in Rats by the Related Brain Metabolite Quinolinic Acid," *Neuroscience Letters*, 48:273–278, (1984).

Andine, P., et al., "The Excitatory Amino Acid Antagonist Kynurenic Acid Administered After Hypoxic–Ischemia in Neonatal Rats Offers Neuroprotection," *Neuroscience Letters*, 90:208–212, (1988).

Merck Manual, 14th Ed., p. 1362–1363 (1982).*

Medline Abst. 88319420 of Neurosci Lett: 90 :208–12 (1988).*

Chem Abst. 111(10):84105 of WO8807851 (1985).*

Chem Abst. 111(19) : 173999 of EP. 303387(1989).*

* cited by examiner

Primary Examiner—Kevin E. Weddington
(74) *Attorney, Agent, or Firm*—Hamilton, Brook, Smith & Reynolds, P.C.

(57) ABSTRACT

Neurological diseases such as Huntington's caused by the toxic effects of excetatory amino acids are alleviated by administering metabolic precursors of kynurenic acid to afflicted individuals. These metabolic precursors include kynurenine and tryptophan. Since the amount of kynurenic acid in Huntington's Disease patient's brains is less than that in normal individuals and such decrease is associated with the lesions found in the formation of the lesions. This occurs because kynurenic acid is an inhibitor of excitatory amino acid interactions at their receptors.

8 Claims, 10 Drawing Sheets

TREATMENT OF NEUROLOGICAL DISEASES BY INCREASING BRAIN CONCENTRATIONS OF KYNURENIC ACID

RELATED APPLICATIONS

This is a Continuation of U.S. Ser. No. 07/944,679 filed Sep. 14, 1992, now abandoned, which is a Continuation of U.S. Ser. No. 07/850,096 filed Mar. 12, 1992 now abandoned which is a Continuation of Ser. No. 07/758,743 filed Sep. 12, 1991, now abandoned which is a Continuation of Ser. No. 07/667,966 filed Mar. 12, 1991 (now abandoned), which is a Continuation of Ser. No. 07/582,429 filed Sep. 13, 1990 (now abandoned).

GOVERNMENT SUPPORT

This invention was made with Government support under NINCDS 16367, SBIR 2R44, NS 24112 awarded by the NIH. The Government has certain rights in the invention.

BACKGROUND OF THE INVENTION

Although the gene responsible for Huntington's disease (HD) has been localized to chromosome 4 (Gusella et al., Nature 306:234–238 (1983)), the pathogenesis of the illness remains obscure. One theory is that an "excitotoxic" process may play a role. This theory was originally based on the observation of similarities between kainic acid striatal excitotoxin lesions and the neuropathologic and neurochemical features of HD (Coyle and Schwarcz, Nature 263:244–246 (1976); McGeer and McGeer, Nature 263:512–519 (1976)). Schwarcz et al., Science 219:316–318 (1983) found that quinolinic acid striatal excitotoxic lesions are also similar to those of HD. Beal and co-workers found that this compound, and other agonists acting at the N-methyl-D-aspartate (NMDA) subtype of excitatory amino acid receptors, could more accurately replicate the neurochemical and histologic features of HD (Beal et al., Nature 321:168–171 (1986) and Synopse 3:38–47 (1989)). The possibility that an excitotoxin acting at NMDA receptors is involved in HD has been strengthened by the finding of Young et al., Science 241:981–983 (1988) that NMDA receptors are profoundly depleted in HD. Moreover, this appears to be an early phenomenon in the course of the illness.

Although there have been many researchers investigating HD, little is known about its etiology and possible approaches to lessening or avoiding its effects.

SUMMARY OF THE INVENTION

The present invention relates to a method for treating neurological diseases that are caused by excitatory amino acid induced lesions in the brain. The treatment can be either prophylactic in nature or to alleviate the symptoms of such diseases. The lesions are thought to be caused by an abnormally elevated number of interactions at the excitatory amino acid receptors by these excitatory amino acids or their agonists.

The present invention provides the treatment by administering a substance to the subject individual that increases the brain concentration of a metabolic precursor to an endogenous blocker of the toxic excitatory amino acid interactions at their receptors. The blocker acts either as an antagonist or as an allosteric inhibitor at the excitatory amino acid receptor.

In particular, the endogenous blocker is kynurenic acid. Metabolic precursors to kynurenic acid include kynurine (the immediate metabolic precursor of kynurenic acid) and tryptophan. These precursors can be administered to an individual by direct application into the brain or, preferably, by peripheral loading. Such loading can be accomplished by ingestion or by injection, e.g., intravenously or intraperitoneally. The loading causes the metabolic precursor to cross the blood-brain barrier into the brain where they are metabolically transformed into the endogenous blocker, i.e., kynurenic acid. Alternatively, the metabolic precursors can be stimulated to cross the blood-brain barrier by loading the individual with substances that alter the ratio of protein bound precursor (kynurenine or tryptophan) to free precursor such that more free precursor is available to cross the blood-brain barrier. The substances include neutral amino acids and carbohydrates.

The invention also includes the increase in amount or activity of kynurenine aminotransferase in the brain of the subject individual. This enzyme is responsible for forming kynurenic acid from kynurenine. An increase in its amount or activity will yield increased concentrations of kynurenic acid from the available stores of its metabolic precursors.

BRIEF DESCRIPTION OF THE DRAWINGS

**p<0.01 by Mann-Whiteney U test for comparison with controls. The enzyme at step A is kynurenine transaminase.

DETAILED DESCRIPTION OF THE INVENTION

A large number of studies now suggest that cellular communication using excitatory amino acids can be transformed by disease into a mechanism of cell destruction. The major excitatory neurotransmitter in the mammalian central nervous system is L-glutamate, which is present in nerve terminals in millimolar concentrations.

Normally extracellular levels of glutamate are elevated to high levels only in a brief and spatially localized fashion associated with normal synaptic transmission. Under pathologic circumstances, such as hypoxia or hypoglycemia, levels may become dramatically increased. In addition, several other compounds are present in mammalian brain which act at excitatory amino acid receptors and which can kill neurons. The precise cellular mechanisms underlying neuronal destruction following excitotoxin lesions are unknown.

Figure 1:
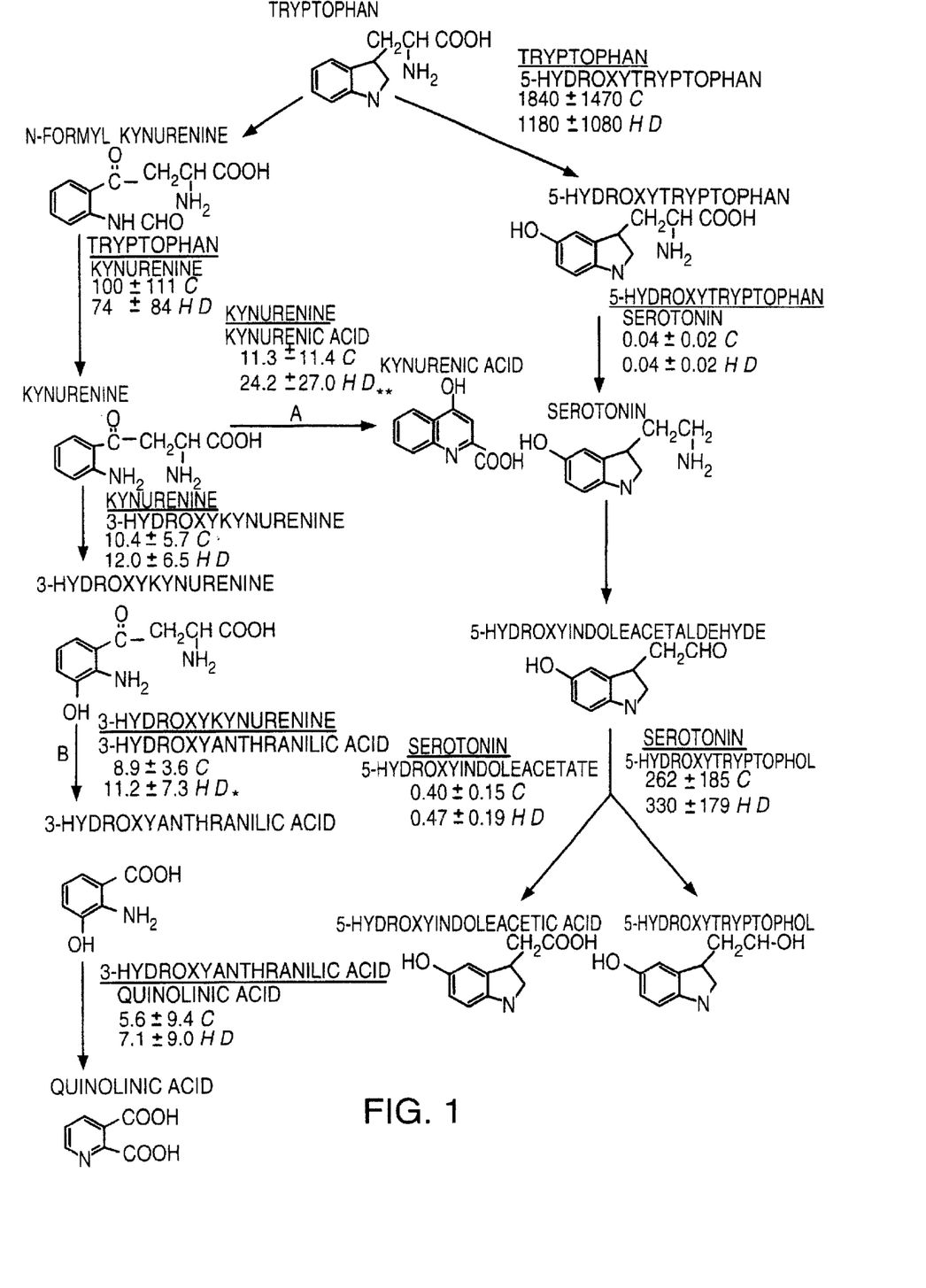
FIG. 1 is a schematic representation of tryptophan metabolism. The ratios of precursors to metabolites (mean±SD values) for controls (c) and HD patients (HD) are shown at each step. There was a significant twofold increase in the ratio of kynurenine to kynurenic acid in HD.

Tryptophan metabolism in the brain follows two branches, as shown in FIG. 1. One leads to serotonin (FIG. 1). The other branch is the kynurenine pathway which leads to both quinolinic acid, a putative endogenous excitotoxin, and kynurenic acid, an excitatory amino acid antagonist. 3-Hydroxyanthranilic acid oxidase, the synthetic enzyme for quinolinic acid, is markedly (3–5 fold) increased in HD; however quinolinic acid concentrations in both HD postmortem tissue and cerebrospinal fluid are unaltered.

Kynurenic acid is an endogenous inhibitor of excitatory amino acid neurotransmission. A broad spectrum antagonist of excitatory amino acid (EAA) receptors is kynurenic acid, which can antagonize electrophysiological responses to N-methyl-D-aspartate (NMDA) and kainic acid (KA) receptor agonists, and to a lesser degree quisqualate (QUIS) receptor agonists. Recent evidence suggests that kynurenic acid acts at both the glycine allosteric site and the agonist recognition site on the NMDA receptor complex, as well as at non-NMDA receptors.

Synthesis of kynurenic acid from L-kynurenine is catalyzed by kynurenine aminotransferase (EC 2.6.1.7), which has been extensively studied in mammalian liver, kidney and intestine (Mason, 1954; Mason, 1957; Mason, 1959; Mason and Gullekson, 1960; Noguchi et al., 1973; Okuno et al., 1980) and has also been found in rat brain (Minatogawa et al., 1974). Recently the presence of kynurenic acid in mammalian brain has been unequivocally demonstrated (Swartz et al., 1990; Carla et al., 1988; Moroni et al., 1988 a, b; Turski et al., 1988). Using brain slice preparation in vitro Turski and colleagues (1989) demonstrated the synthesis and release of kynurenic acid when L-kynurenine is added to the incubation media; however no kynurenic acid could be found in the absence of added L-kynurenine (in all cases >25 $\mu$M).

Both in vivo and in vitro kynurenic acid reduces NMDA, kainate and quisqualate-induced neuronal excitation. It can block synaptic transmission in the cerebral cortex, hippocampus, striatum and spinal cord. In the striatum, kynurenic acid is protective against both kainic acid and quinolinic acid neurotoxicity. It also protects against kainic acid neurotoxicity in the nucleus basalis, prevents seizures induced by excitatory amino acid agonists, partially protects in a rat model of cortical infarcts, and reduces brain edema in neonatal anoxia. Kynurenic acid exerts its effects on the NMDA receptor both as a competitive antagonist, and by competing for the glycine allosteric site on the NMDA receptor complex. It appears to be 4–5 fold more potent at the glycine site than as a competitive antagonist. It is, therefore, more likely to act at the glycine site in low concentrations. Glycine is necessary for and potently enhances NMDA responses at this site.

The enzyme which synthesizes kynurenic acid is kynurenine transaminase. This enzyme is present in rat brain. There are at least 2 isoenzymes which can act as kynurenine transaminases in human brain. These enzymes are thought to be localized to glial cells, since slices of ibotenate lesioned striatum show a higher rate of kynurenic acid formation than control striatum. Kynurenic acid is widely distributed in human brain with the highest levels in the caudate and lower levels in the cerebellum.

A mechanism which results in excitation neuronal death in neurodegenerative illnesses is a deficiency of kynurenic acid. It has been shown, as described herein, that there is a 2-fold increase in the ratio of kynurenine to kynurenic acid in HD putamen. Significant reductions in kynurenic acid concentrations in HD CSF and 7 cortical regions were also observed. Since there is no metabolism of kynurenic acid in brain tissue, these findings indicate there is reduced formation of kynurenic acid in HD as compared with controls. Reduced levels of kynurenic acid are unlikely to be secondary to neuronal loss of gliosis, since ibotenate lesioned striatum results in increased formation of kynurenic acid at one week. It is likely that kynurenine transaminase activity is reduced in HD. Consistent with this possibility is the finding that kynure-nine and kynurenic acid were much more tightly correlated with tryptophan in HD than in controls. An enzyme deficiency can make the pathway more substrate dependent so reduced formation of kynurenic acid results in increased activation of NMDA receptors, and subsequent excitotoxic mediated neurodegeneration.

Since kynurenic acid is an endogenic blocker of excitatory amino acid receptors, precursor loading can exert neuroprotective effects. Kynurenine is taken up into brain by the neutral amino acid transporter.

As described herein, it has now been shown that the brain synthesizes and releases kynurenic acid and that cerebral extracellular fluid (ECF) levels of this neuroprotective agent can be manipulated pharmacologically. In particular, it has been shown that administration of L-kynurenine or of L-tryptophan results in increased cerebral ECF levels of kynurenic acid.

As a result of the work described herein, it is possible to increase kynurenic acid levels in brain tissue, in which it can act to inhibit excitatory amino acid receptors and influence effects of EAA on the brain. For example, brain kynurenic acid levels can be increased in an individual with a neurological condition, such as HD, by administering to the individual kynurenine, a kynurenine analogue, tryptophan or a combination thereof. This can be effected in a variety of ways. For example, increased levels of tryptophan and/or kynurenine or a kynurenine analogue can be administered orally (e.g., in the diet) or parenterally. For example, 5-chlorokynurenine may be given as a precursor for 7-chlorokynurenic acid, which is a kynurenic acid analogue with increased potency against brain excitatory amino acid receptors. In this invention, it is shown that kynurenine loading can increase kynurenic acid concentrations by up to 37 fold, into a range which may have activity at the glycine allosteric site on the NMDA receptor.

Kynurenine can be metabolized to quinolinic acid in the brain and in the periphery. This metabolism involves the enzymes kynureninase and 3-hydroxyanthranilic acid oxidase (FIG. 1). Inhibitors of these enzymes are available. It may therefore be possible to administer inhibitors of these enzymes in conjunction with kynurenine, a kynurenine analogue, tryptophan or a combination thereof in order to increase kynurenic acid formation in the brain, without concomitantly increasing quinolinic acid production. This is useful as a novel therapeutic approach to HD and other disorders in which excitotoxin mechanisms have been implicated. It has been shown that even without administration of such an enzyme, very high doses of kynurenine result in only a 6 fold increase in brain tissue levels of quinolinic acid, suggesting there is an inherent biological mechanism that limits the production of quinolinic acid in the brain. Although the present invention has been described in terms of a specific endogenous blocker of excitatory amino acid receptors, a precursor of another endogenous blocker can be used in a similar manner to treat an individual with a neurological disease.

The present invention is illustrated by the following examples, which are not intended to be limiting in any way.

EXAMPLE 1

Materials and Methods

Postmortem brain tissue was obtained from HD and control patients. All the HD patients had typical clinical features, a positive family history, and degeneration in the basal ganglia meeting neuropathologic criteria for the illness. Controls were free of neurologic illness and showed no neuropathologic abnormalities. The postmortem intervals were well matched; however, the HD patients were significantly (p<0.05) younger than the controls. There was a higher incidence of death from pneumonia and of neuroleptic drug usage in the HD patients. The brains were bisected at the time of autopsy and stored frozen at $-70°$ C. until dissected at $-10°$ C. on a freezing cold plate as previously described. The entire putamen was dissected, and tissue was diced, mixed, and stored at $-80°$ C. in cryotubes.

Samples aliquots of between 100 and 300 mg were weighed and placed in 1 ml of ice-cold 0.1 M $HClO_4$. Samples were then sonicated on ice for 20 s and centrifuged 10,000 g for 10 min at $4°$ C. The upernatants were stored frozen at $-70°$ C. Protein content determinations were made on the pellet using a fluorometric assay. The stored samples were subsequently thawed to 0 C. under nitrogen, and 100-$\mu$l aliquots were placed in conical 300-$\mu$l autosampler vials before analysis. Sample pools were created for assay evaluation by combining 50-$\mu$l aliquots of each sample. Control standards of 37 components were prepared at the approximate physiological levels found in preliminary assay of the pools, and augmented pools were prepared at approximately four times physiological levels.

Sample analysis was performed using HPLC with a 16-sensor CEAS. The fundamental concept of the 16-sensor array cell is that a series of coulometric electrodes set at incrementally increasing potentials provides a second, virtually instantaneous stage of separation of the eluant peaks. Because compounds are completely oxidized at a given potential, the subsequent sensors are essentially independent. A given compound can, therefore, be described not only by retention time, but also by a potential at which it oxidizes. In practice, compounds show a dominant detector response with a leading and following response, which is typically 10–30%. The ratio of response across three electrodes is highly characteristic of a particular compound. If a correct ratio is not obtained, this suggests that a coeluting contaminant may be present. The complete apparatus (ESA model CEAS 55–0650) consists of a refrigerated autosampler (ESA model 460) and two HPLC pumps (ESA model 420), controlled by an AT-compatible computer (Epson Equity III), with a column sensor compartment temperature controllable from 15 to $40°$ C. to $\pm 0.01°$ C. In current practice, the data from an analysis are stored as raw information in a file for each sensor. Each sensor file is then searched automatically for peaks, and the report for a particular sample is organized into a time-potential map of peak response. Sample time-potential maps are then merged with standard maps, and analytical values are calculated based on a match of retention times and peak ratios. Except where mobile phases were produced in bulk (ESA CEAS mobile phases A and B), all mobile phases were produced in 10-L batches from distilled Milli Q water, and salts were extracted with chloroform, propanol, and methanol. Columns (ESA HR80; 3 $\mu$m particle size, 15 cm long, C18, Teflon lined) were selected from a lot of 50 for $\pm 2\%$ equivalence in theoretical plates.

Because of the complexity and variability of human tissue extract samples, three separate methods were used to create and verify the analytical data included in the database. Methods were selected based on several criteria. First, a method was centered on a particular group of compounds to provide optimal resolution and sensitivity across the variability encountered among all samples. Second, methods were selected for overlap of compounds quantified to provide additional analytical verification and certainty of peak purity. Third, analytes were selected that provided additional feedback on noninstrumental variables in the total analytical system. For this purpose, ascorbate was monitored on all assay performances to control for possible oxidative degradation, and guanine and adenine were checked for sonication degradation effects.

All samples were initially assayed with a previously reported isocratic method, which was optimized for the resolution of 3-hydroxyanthranilic acid, 3-hydroxykynurenine, and kynurenine. It also gave accurate ratios for 25 other compounds in at least 80% of the individual samples. The primary method limitation was the late elution of tryptophan. Samples in which any analyte ratios were suspect were then assayed by a gradient method, with mobile phase A running to mobile phase B over a 65-min period. The A mobile phase is 0.1 M $NaH_2PO_4$ (pH 3.21) adjusted with phosphoric acid, 10 mg/L of dodecyl sulfonic acid, and 5 mm nitrilotriacetic acid; the B mobile phase is 50% methanol and 50% 0.1 M $NaH_2PO_4$ (pH 3.35) adjusted with phosphoric acid, 50 mg/L of dodecyl sulfonic acid, and 5 mM nitrilotriacetic acid The sensors were set from 0 to 900 mV at 60 mV intervals. This method provided overlapping results for all analytes in the first assay, as well as tryptophan values.

Neither of the first two assays provided full resolution of kynurenic acid. Consequently, a third method was used with an A mobile phase of 0.5 M $NaH_2PO_4$ (pH 6.26) and a B mobile phase of 50% methanol and 50% 0.05 M $NaH_2PO_4$ (pH 6.26) with 500 mg/L of tetrabutyl ammonium hydroxide. A gradient was run to 100% B over a 60-min period. The sensors were set from 0 to 1,200 mV at 80-mV intervals. The maximal response for kynurenic acid was on sensor 14 (1,040 mV), with the secondary response on sensor 15 (1,120 mV). The precision of kynurenic acid level measurements of 20 bracketing standard assays was ±1.76% coefficient of variation. This method provided overlapping values for tryptophan, kynurenine, homovanillic acid, 5-hydroxyindoleacetic acid, and 4-hydroxyphenyllactic acid. For all methods, two 8-×0.45-cm, 3-$\mu$m-particle size, C18 ESA HR80 (Teflon) columns were used in series at a temperature of 35° C.

For each set of samples, an initial evaluation of control standards was made to verify that they were assayed within acceptance limits of ±2% retention time, ±4% response, and ±20% ratio accuracy as compared with standards. The response ratios for standards are defined as the ratios of the dominant sensor to the leading and following sensors. If the response ratios of unknown peaks are within ±20% of those of standards, then quantification is performed by summing the values from all three sensors. Assays were performed using the sequence of control standard, eight samples, control standard. Samples were assayed blind, and pools and augmented pools were included as samples for postassay evaluation of overall assay validity. Initial results, in nanograms per milliliter of extract, were calculated from averaged response of the standards bracketing each group of samples. Twenty-six pools, one for each assay performance, were used to determine the coefficient of variation (SD/mean value) for each compound analyzed.

Final results were calculated in nanograms per milligram of protein after correction of the extraction volumes for the fluid concentration of the brain tissue, using 0.82 times milligrams of wet weight equals microliters contributed. Sensitivity limits were defined as the amount of analyte that could be detected with an SD of ±0.5 times the amount injected. These limits varied depending on the compound but were typically 1–5 pg on column (0.001–0.005 ng/mg of protein). These values were three to 30,000-fold lower than the lowest values encountered in the data set.

After the analyses were organized in a database, values for any compound or ratio of compounds that were >3 SD from the mean were tested for rejection by a regression analysis protocol using all the information in the database. Regression equations were calculated for each compound versus all other compounds, excluding the row or sample containing the suspect value. The regression coefficients for the suspect compound were then used to calculate its predicted value from all other compounds in the sample. Rejection criteria were then based on the suspect value minus the regression calculated value being >3 SD of the mean.

CSF samples were obtained by lumbar puncture from consenting hospitalized patients or outpatients undergoing diagnostic procedures. Control CSF specimens were obtained from 50 patients undergoing myelography or being evaluated for fever or headache. In all control cases, neuroradiologic studies and neurologic examination were normal. These patients had no history of neurologic illness, and CSF examinations showed normal CSF glucose, protein, and cell counts. CSF samples were obtained from 23 patients showing typical clinical manifestations of HD and in which there was a family history of the illness. Nine of the HD patients were receiving neuroleptic drugs. In addition, specimens were obtained from nine patients with a clinical diagnosis of Alzheimer's disease and six patients with Parkinson's disease. Additional disease controls were 13 patients with herniated lumbar discs at myelography and 12 patients with ischemic strokes. CSF measurements of kynurenic acid levels were made by HPLC with fluorometric detection (Swartz et al., 1990).

Data were analyzed using the Mann-Whitney U test, the Kruskall-Wallis test, linear regression, and multiple regression analysis. Results are expressed as mean ±SD values, except in Table 1, where SEM is used. After an initial analysis, confirmatory measurements were obtained of both kynurenine and kynurenic acid levels with the hypothesis that an abnormality was present in HD. Other statistical comparisons were accepted at the $p<0.01$ level to take into account the per-experiment error rate.

All samples were analyzed blind and later decoded. Of the 25 compounds analyzed, significant differences occurred in six. Serotonin, 5-hydroxytryptophan, and 5-hydroxyindoleacetic acid levels were significantly increased by 63, 57, and 37%, respectively, in HD. Guanosine concentrations were significantly reduced by 21% in HD. Kynurenic acid concentrations were decreased 38% in HD putamen, but this did not reach significance ($p=0.07$) owing to the large variance of measurements in both controls and HD patients. Compounds were also analyzed by dividing their content by the combination of uric acid added to xanthine. This has the advantage of a divisor closely related to both protein and wet weight obtained from the same method of analysis. This method of data analysis tightened the variance of the data and reulted in more significant statistical differences among several compounds, as well as significant increases in cysteine, 4-tyrosine, and 3-methoxytyramine levels, yet no change in guanosine content.

The individual components of tryptophan and tyrosine metabolism were examined in further detail. Not only were levels of the individual components measured, but the ratios of precursor compounds to their metabolites were calculated, to assess the rate of turnover through various parts of the pathways. These ratios have the advantage that they are not affected by the tissue shrinkage and gliosis that occur in HD.

The metabolism of tryptophan is shown in FIG. 1. Tryptophan concentrations were unaltered in HD; however, there were significant increases in 5-hydroxytryptophan, serotonin, and 5-hydroxy-indoleacetic acid concentrations as noted above. The ratios across the serotonin branch of the pathway were unchanged. Concentrations of individual components of the kynurenine pathway were not significantly changed in HD. The ratios of several precursors to metabolites along the kynurenine pathway were significantly altered in HD. The ratio of kynurenine to the sum of its metabolites was significant ($p<0.01$) twofold increase in the ratio of kynurenine to kynurenic acid in HD. Pathologic grading was available on some but not all of the HD patients (Vonsattel et al., 1985). In nine grade 2 patients, the ratio of kynurenine to kynurenic acid was 27.2±13.5, whereas in 12 grade 3 patients, the ratio was 23.8±5.7, a value not differing significantly from that in the grade 2 patients.

Other significant ratios of interest are shown in Table 1. Although there was no alteration in the ratio of tyrosine to the sum of its metabolites, there was a significant decrease in the ratio of tryptophan to its metabolites in HD. This suggests increased overall tryptophan metabolism in the HD patients. In contrast, the ratio of kynurenine to the sum of its metabolites was significantly increased in HD, a finding suggesting reduced metabolism through this pathway. The ratio of 3-hydroxykynurenine to kynurenic acid was significantly increased, similar to the ratio of kynurenine to kynurenic acid, although not quite as great in magnitude. The contents of cysteine metabolites were significantly in HD putamen.

TABLE 1

Other Significant Ratios

|  | Controls | HD |
|---|---|---|
| Tryptophan/sum of its metabolites | 12.8 ± 10.3 (30) | 7.4 ± 4.7 (26)* |
| Kynurenine/sum of its metabolites | 6.5 ± 3.5 (30) | 8.7 ± 4.6 (26)* |
| Cysteine metabolites/ xanthine and uric acid | 1.9 ± 0.4 (34) | 2.6 ± 0.7 (30)* |
| 3-Hydroxykynurenine/ kynurenic acid | 1.4 ± 1.6 (30) | 2.5 ± 2.7 (26)* |

*p < 0.01 by Mann-Whitney U test.

The correlation of kynurenic acid versus age in HD was r–0.356, p=0.074, whereas in controls it was r=0.141, p=0.47. Guanosine was significantly correlated with age in HD (r=0.387, p=0.038) but not in controls (r=0.257, p=0.156). No other compounds correlated significantly with age. In addition, none of the compounds examined showed significant correlations with postmortem intervals. There were no significant differences in either levels of tryptophan metabolites or their ratios in HD patients who were receiving or not receiving neuroleptic drugs.

Figure 2:
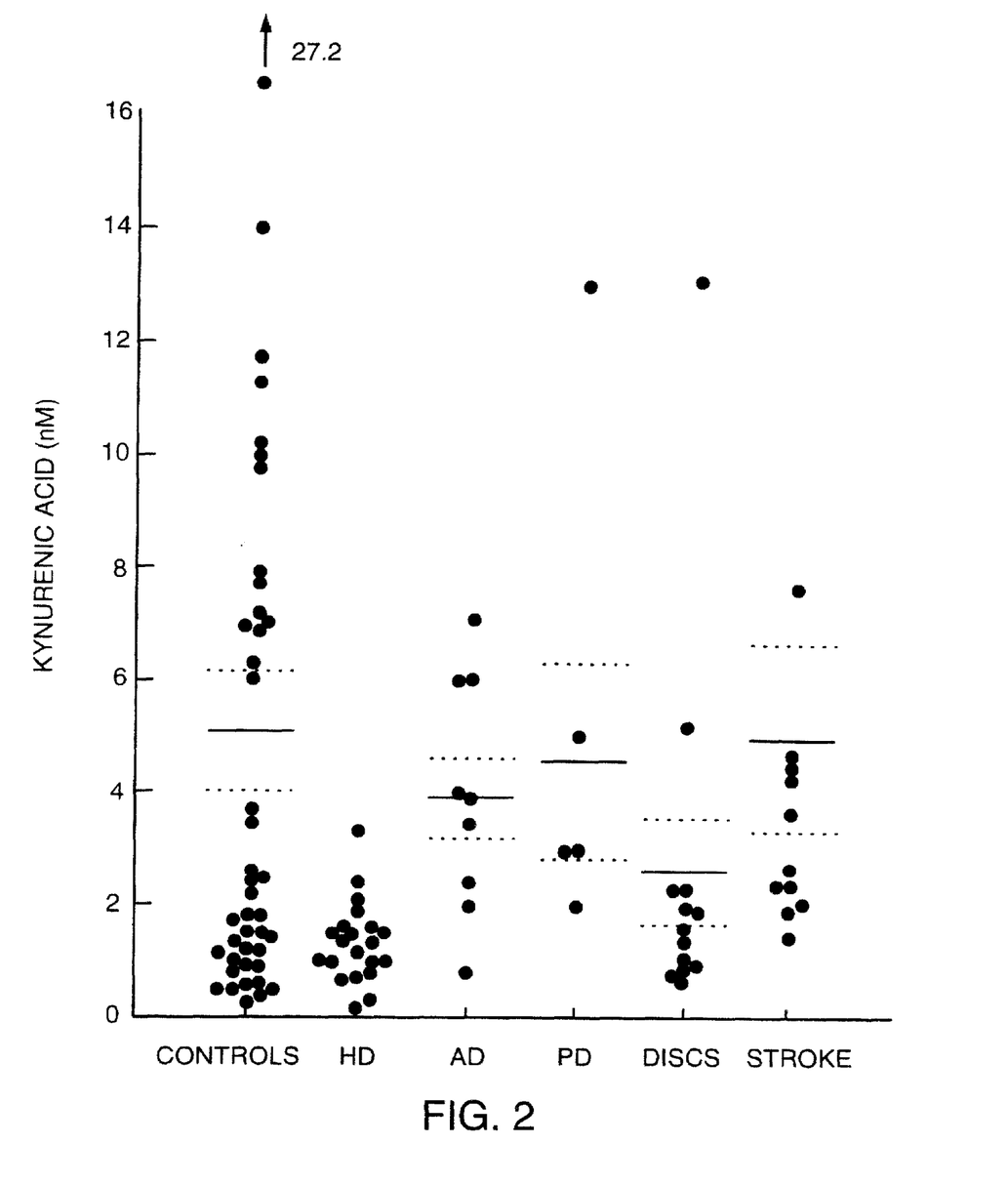
FIG. 2 shows CSF concentrations of kynurenic acid in controls, HD patients, and patients with other neurologic illnesses. The concentrations in HD were significantly reduced (p<0.001) as compared with controls. The other disease states did not differ significantly from controls. AD, Alzheimer's disease; PD, Parkinson's disease.

The result of CSF studies are shown in FIG. 2. The concentrations (nM) of kynurenic acid in the various groups were as follows: controls, 5.10±1.04; HD, 1.29±0.14; Alzheimer's disease, 3.93±0.71; Parkinson's disease, 4.59±1.75; discs, 2.64±0.93; and ischemic strokes, 5.04±1.66. The Kruskall-Wallis test showed that the groups were significantly different (H=24.61, p=0.0004). Posthoc analysis showed that only the HD patients differed significantly from controls. The age of the controls (43.8±3.2 years) did not differ significantly from that of the HD patients (45.5±4.1 years), whereas the Alzheimer's (76.7±4.7 years) disease patients were significantly older. Kynurenic acid concentrations were significantly correlated with age in the controls (r=0.49, p=0.0003) but not in any of the other groups. HD patients taking neuroleptic medications had CSF kynurenic acid concentrations that did not differ significantly from those in patients not taking these medications (1.26±0.17 vs. 1.37±0.31 nM). The CSF kynurenic acid concentrations in the HD patients did not correlate significantly with disability scores, age of onset, or duration of disease.

EXAMPLE 2

Experimental Methods

Male Sprague-Dawley rats (200–300g) were purchased from Charles River Laboratories (Wilmington, Mass.) and maintained under standard conditions with ad lib access to water and Rodent Lab Chow 5001 (Purina Mills, Inc.) under a 12 hour dark/light cycle. All experiments were started in the morning, between 7:00 and 8:00 a.m. Rats were anesthetized with freshly prepared chloral hydrate (350 mg kg$^{-1}$ i.p.) with small additional doses throughout experimentation to maintain stable anesthesia. Anesthetized rats were placed in a Kopf stereotaxic frame and maintained on a homeostatic heating pad at 37° C. Dialysis probes were implanted into anterior striata (either unilaterally or bilaterally) through small burr holes drilled in the skull at the coordinates: 0.5 mm anterior to bregma, 2.6 mm lateral to midline and 7.0 ventral to skull surface. Accurate placement of probes was verified postmortem by gross and light microscopic visualization of coronal sections cut through and on either side of the probe path.

Microdialysis:

The dialysis probes were of concentric design and had a 4 mm length of exposed membrane so that the diffusion surface spanned the entire dorsoventral coordinates of the rat striatum. Hollow dialysis fibers (5 kDa cut-ff; Cuprophan, Hospal, Edison, N.J.) were sealed at one end with epoxy resin (Devcon, Danvers, Mass.). A length of hollow vitreous silica fiber (0.17 mm outer diameter, Anspec, Mich.) was inserted into the dialysis tube flush to the sealed end. The dialysis tubing with the vitreous silica fiber in situ was then inserted through a length of 23 gauge stainless-steel tubing into which another length of vitreous silica fiber (outlet) had been placed. Both ends of the 23 gauge tubing were sealed with epoxy resin, with the dialysis membrane protruding from one end of the probe. The length of exposed membrane surface was controlled by coating the dialysis membrane with epoxy resin. The probe was perfused using a Carnegie Medicin microperfusion pump (model CMA/100) via PE-50 tubing. The perfusate consisted of an artificial extracellular fluid (ECF) containing the following: 135 mM Na$^+$, 2.8 mM K$^{+H,\ 1.0\ mM\ Mg2+}$, 1.2 mM Ca$^{2\ +}$, 200 uM ascorbic acid, 2.0 mM phosphate at pH 7.4. The flow rate in all experiments was 2.0 µl min$^{-1}$, with fractions collected at 30 minute, (L-kynurenine studies) or 60 minute (L-tryptophan studies) intervals. Probes were calibrated in vitro by placing them in standard solutions containing 20.0 and 200.0 mM authentic kynurenic acid and measuring the recovery of kynurenic acid in the dialysate. The in vitro recovery of all probes used (N=10) was 11.2±0.4% (mean ±S.E.M.).

Analytical Measurements of Kynurenic Acid

Kynurenic acid was measured using high performance liquid chromatography (HPLC) with fluorescence detection. The HPLC system used for analysis of kynurenic acid consisted of the following: pump A- Waters Model 510 Solvent Delivery System, pump B- Waters M45 Solvent Delivery System, a BIORAD Automatic Sampler (refrigerated) Model AS-48, a Waters 470 Scanning Fluorescence Detector, a Shimadzu C-R5A Chromatopac Integrator and a BBC Goerz Metrawatt SE-120 chart recorder The HPLC-fluorescence method utilized a mobile phase of 4.5% acetonitrile, 50 mM sodium acetate, pH 6.20 (adjusted with glacial acetic acid), pumped through a 8 cm HR-80, C-18, 3 u reverse phase column (ESA Inc.) at a flow rate of 1.0 ml min.$^{-1}$. Zinc acetate (0.5 M; not pH adjusted) was delivered post-column at a flow rate of 1.0 ml min.$^{-1}$. The injection volume was 50 µl. The fluorescence detector was set at an excitation wavelength of 344 nm (18 nm band width) and an emission wavelength of 398 nm (18 nm band width). The retention time of kynurenic acid under these conditions was 4.3 min., with a sensitivity of 15.0 fmol injection$^{-1}$ (signal:noise ratio=5). For dialysate measurements, the recovered dialysate (60 µl) was diluted 1:1 with fresh articificial ECF and 50 µl directly injected onto the HPLC system. Aminooxyacetic acid (AOAA), L-kynurenine and L-tryptophan did not interfere with the measurements of kynurenic acid when added to standard solutions or ECF containing exogenous or endogenously synthesized kynurenic acid. Plasma kynurenic acid measurements were made using the same HPLC system with minor modifications in sample preparation procedures. Freshly collected blood (200 µl) was centrifuged at 12,000 rpm for 10 minutes. The resulting plasma (50 µl) was separated off, diluted to 1.0 ml with 0.5 M CHlO$_4$ and centrifuged at 12,000 rpm for 10 minutes to remove precipitated protein. 50 µl of the resulting supernatant was directly injected onto the HPLC system.

Systemic Precursor Loading Studies: Effects on Striatal ECF Kynurenic Acid

In several experiments, precursors (L-kynurenine or L-tryptophan) were administered peripherally while striatal ECF was sampled. Dialysis probes were implanted for a minimum of 1.5 hours before baseline fractions were collected. Three 30 minute fractions were collected before any manipulation was attempted. L-kynurenine sulfate and L-tryptophan (Sigma, St. Louis, Mo.) were dissolved in sterile 0.9% saline (pH 7.4) and administered intraperitoneally (i.p.) in a volume of 3–4 ml per kg. One group of rats received either saline along (N=5) or L-kynurenine at doses of 100 mg $kg^{-1}$ (N=4), 75 mg $kg^{-1}$ (N=4), 50 mg $kg^{-1}$ (N=4), 25 mg $kg^{-1}$ (N=2). The quantity of L-kynurenine sulfate given was calculated as the free base. Another group of rats received either saline along (N=4) or L-tryptophan 100 mg $kg^{-1}$ (N=5). Microdialysis was continued for up to 4 hours at 30 minute intervals when L-kynurenine was given and for 10 hours at 1 hour intervals when L-tryptophan was given.

Cerebral Precursor Administration Studies: Effects on Striatal ECF Kynurenic Acid In order to determine which reactions of the kynurenine pathway, leading to kynurenic acid, exist in brain, we compared the ability of centrally applied precursors to increase striatal ECF concentrations of kynurenic acid Dialysis probes were implanted into rat striata for a minimum of 1.5 hours before baseline fractions were collected. After three 30 minute fractions were collected to establish basal concentrations of kynurenic acid, artificial ECF containing either 100 $\mu$M L-kynurenine (N=7) or 100 $\mu$M L-tryptophan (N=10) was perfused through the dialysis probe for the next 2.5 hours (when L-kynurenine was administered) or 5 hours (when L-tryptophan was administered). Fractions were collected every 30 minutes and kynurenic acid concentrations determined.

Systemic Precursor Loading Studies: Effects on Plasma Kynurenic Acid

We compared the induction of peripheral kynurenic acid formation after administration of L-kynurenine to the effects of L-kynurenine on intracerebral kynurenic acid synthesis. Rats were cannulated with intrafemoral catheters prior to implantation of dialysis probes. Three baseline plasma samples were taken from each rat and six dialysis samples were collected prior to any maniuplation. One group of rats (N=3) received an intraperitoneal infusion of the highest dose of L-kynurenine administered in the precursor ECF studies (100 mg $kg^{-1}$). Subsequent measurements of plasma kynurenic acid determined the magnitude of the increase in plasma kynurenic acid. In a separate group of rates (N=3), kynurenic acid (10 mg $kg^{-1}$) was given i.p. to cause an increase in plasma kynurenic acid of greater magnitude than that observed with L-kynurenine administration. In both groups simultaneous striatal ECF was monitored using microdialysis.

Enzyme Inhibition Studies

In order to establish that the kynurenic acid measured in striatal ECF was synthesized in the CNS rather than transported into the CNS from the periphery, we examined the ability of aminooxyacetic acid (AOAA), an established inhibitor of kynurenine transaminase, to inhibit the kynurenic acid surge produced by peripheral infusion of L-kynurenine. We designed a model with internal controls to negate the effects of variable L-kynurenine absorption from the periphery. Dialysis probes were implanted bilaterally into the striata of five rats. Initially, both probes were infused with artificial ECF. After 1.5 hours of pre-baseline perfusion, three consecutive 30 minute baseline fractions were collected from each probe. After the last fraction was collected, artificial ECF containing either 1.0 mM (N=3 rats) or 2.0 mM (N=2 rats) AOAA was perfused through one probe, while the contralateral probe was perfused with artificial ECF alone, as a control. Both probes were perfused for 1.5 hours (three consecutive 30 minute fractions). After the last fraction was collected L-kynurenine (75 mg $kg^{-1}$) was administered peripherally via an intraperitoneal route. Dialysis fractions were then collected, at 30 minute intervals, for the next 3.0 hours. Ipsi-lateral (AOAA perfused) and contralateral (control) fractions were analyzed for kynurenic acid.

Data Analysis and Statistics

All kynurenic acid values were calculated and expressed in unit of either nM [nmoles/L] or fold-change from baseline levels (mean+S.E.M.). Statistical comparisons were made using repeated measures ANOVE and the Mann-Whitney U test.

Results

Basal levels of kynurenic acid in striatal extracellular fluid were determined in 124 samples collected at 30 minute intervals in 45 anesthetized rats. The basal level of kynurenic acid measured in these dialysates was 1.94±0.12 nM (mean±S.E.M.). After correction for in vitro recovery (11.31% in 10 dialysis probes; see methods section for details) the ECF level of kynurenic acid, under basal conditions, was 17.1±1.1 nM (mean±S.E.M.).

Figure 3:
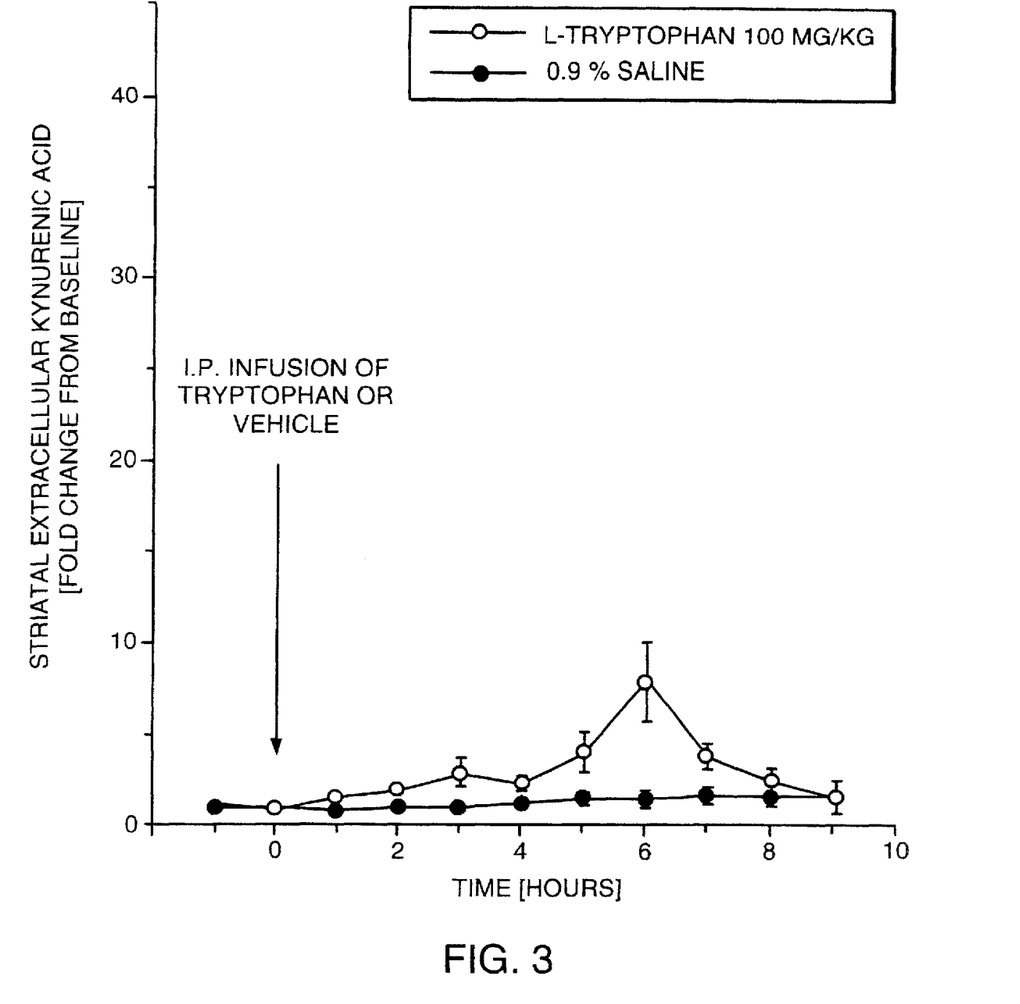
FIG. 3 shows striatal extracellular levels of kynurenic acid following peripheral (i.p.) infusion of saline or L-tryptophan 100 mg kg$^{-1}$. The vertical axis represents the fold change in striatal concentrations of kynurenic acid while the horizontal axis represents time in hours. Time=0 is when the peripheral infusion of L-tryptophan or vehicle occurred. Error bars represent S.E.M.

In initial experiments we examined the effect of peripheral infusion of L-kynurenine or saline (0.9%) on striatal ECF kynurenic acid concentrations. At 25 mg $kg^{-1}$ dialysate levels rose 3.85±0.58 fold (mean±S.E.M.); at 50 mg $kg^{-1}$: 9.47±1.26 fold, at 75 mg $kg^{-1}$: 27.10±4.26 fold and at 100 mg $kg^{-1}$: 37.11±7.04 fold. With the exception of the lowest dose, the response of striatal ECF kynurenic acid peaked between 2.0–2.5 hours after infusion of L-kynurenine. The slope of the rise in striatal ECF kynurenic acid increased with increasing doses of L-kynurenine; however, the difference in slope between the 75 and 100 mg $kg^{-1}$ groups was minimal, suggesting that a maximal rate of precursor uptake, synthesis and release was reached. As illustrated in FIG. 3, administration of L-tryptophan (100 mg $kg^{-1}$ i.p.) also caused striatal ECF concentrations of kynurenic acid to significantly increase. This increase in striatal ECF kynurenic acid was substantially smaller, and occurred at a considerably later time interval, as compared to L-kynurenine administration. Saline infusions (i.p.) had no significant effect on striatal ECF concentrations of kynurenic acid for up to 9 hours (see FIG. 3).

Figure 4A:
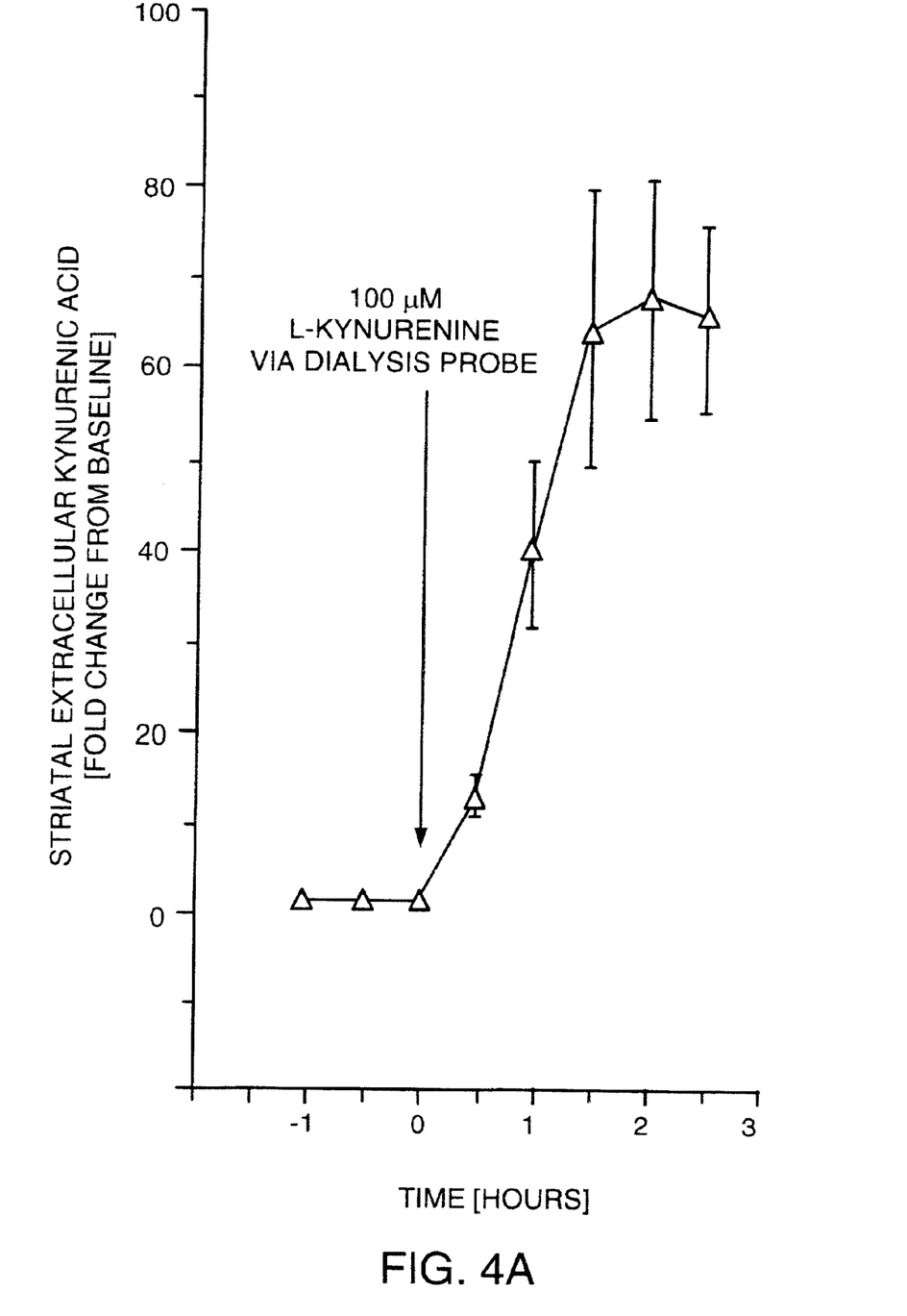
FIG. 4 shows striatal extracellular levels of kynurenic acid following continuous cerebral (via dialysis probe) infusion of 100 μM L-kynurenine (A) or 100 μM L-tryptophan (B). The vertical axis represents the fold change in striatal concentrations of kynurenic acid while the horizontal axis represents time in hours. Time=0 is when L-kynurenine or L-tryptophan infusion via the dialysis probe was started. Error bars represent S.E.M. The inset in B is scaled to 10-fold full scale to show the minimal increase in kynurenic acid that occurred after infusion of L-tryptophan.
Figure 4B:
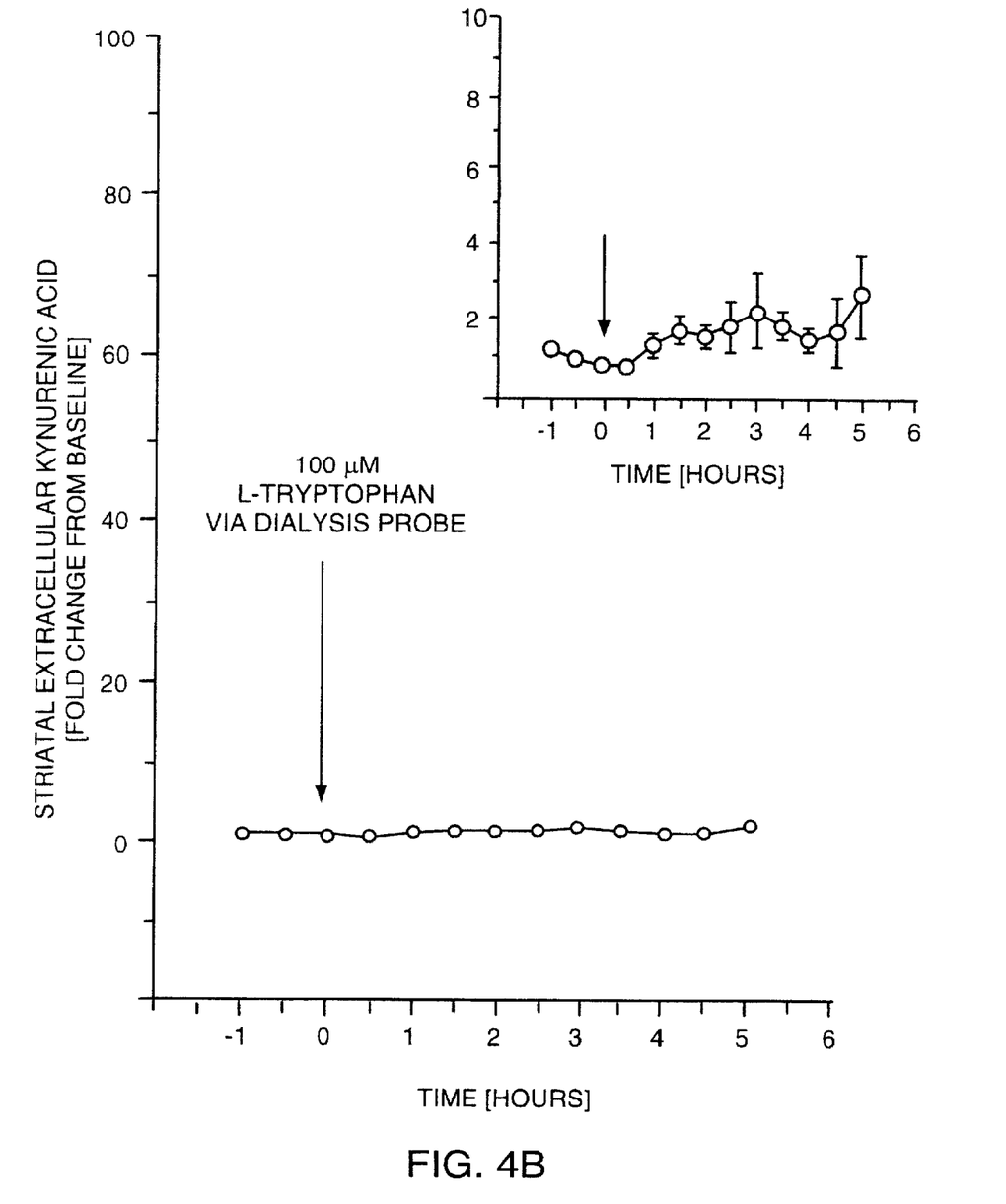

The involvement of cerebral and peripheral metabolism in the synthesis of kynurenic acid from L-tryptophan was examined by comparing the ability of precursors to increase striatal ECF concentrations of kynurenic acid when infused through the dialysis probe directly. As shown in FIG. 4(A), L-kynurenine (100 $\mu$M) infusion via the dialysis probe resulted in marked increases (68.4±13.1 fold) in striatal ECF concentrations of kynurenic acid. L-tryptophan (100 $\mu$M) infusion via the dialysis probe resulted in minimal, non-significant, increases in striatal ECF concentrations of kynurenic acid (see FIG. 4B).

Figure 5:
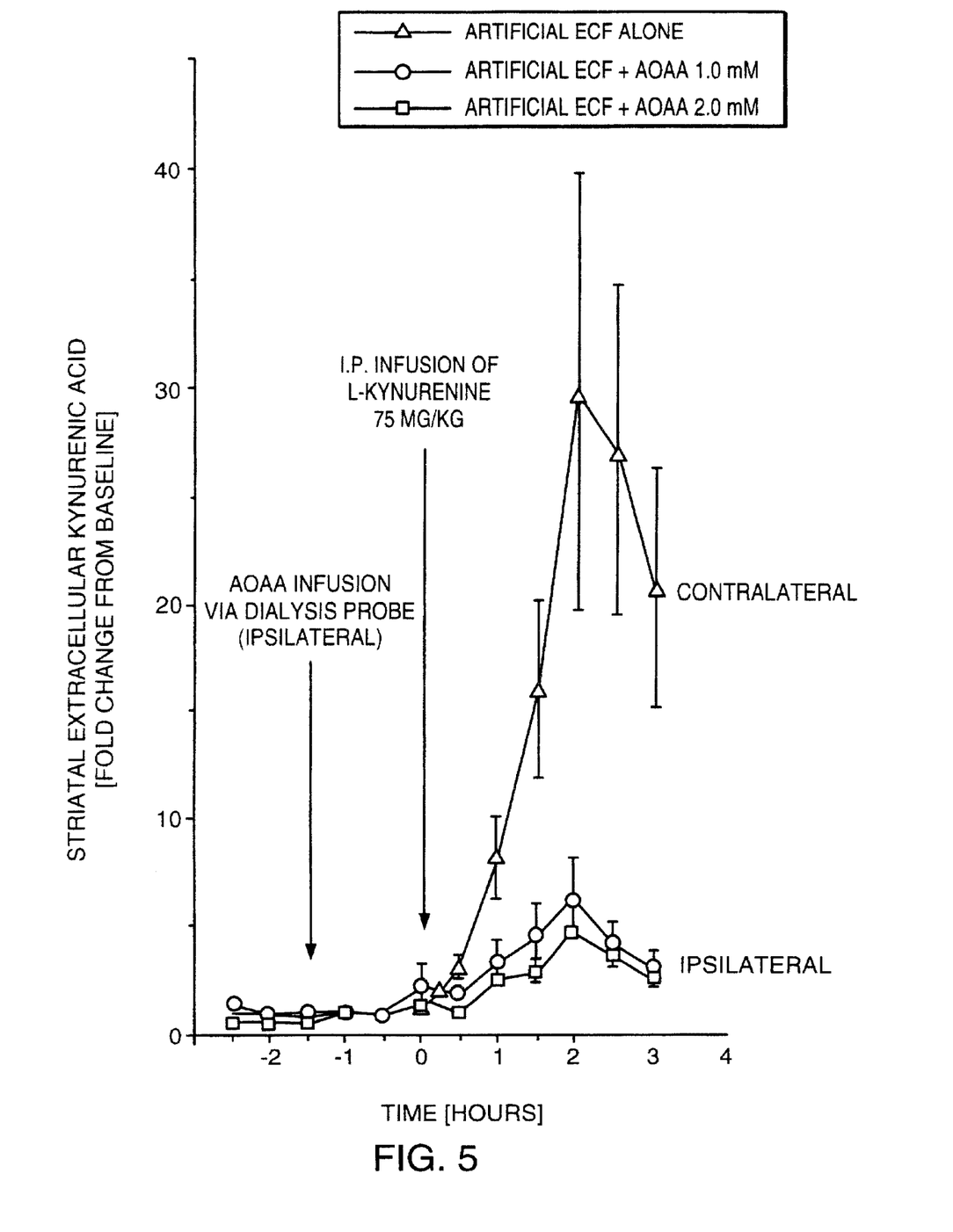
FIG. 5 shows striatal extracellular levels kynurenic acid following peripheral (i.p.) infusion of L-kynurenine 75 mg kg$^{-1}$. One probe (designated ipsilateral) was perfused with artificial ECF (extracellular fluid) containing 1.0 or 2.0 mM aminooxyacetic acid (AOAA) and the other contained standard artificial ECF. The vertical axis represents the fold change in striatal concentrations of kynurenic acid while the horizontal axis represents time in hours. Time=1.5 hours is when infusion of AOAA ipsilaterally was initiated while time=0 when L-kynurenine was injected i.p. Error bars represent S.E.M.

In order to determine whether L-kynurenine was converted to kynurenic acid within the CNS we examined the ability of an inhibitor of kynurenine aminotransferase (applied locally within the central nervous system) to block the striatal ECF kynurenic acid response to peripherally infused L-kynurenine. Aminooxyacetic acid (AOAA) inhibits the immediate synthetic enzyme for kynurenic acid, kynurenine aminotransferase. AOAA containing artificial ECF was infused into one striata and control artificial ECF was infused into the contralateral striata. As illustrated in FIG. 5, when L-kynurenine (75 mg kg$^{-1}$) was given peripherally, the striata receiving the AOAA showed only a small increase in kynurenic acid while the contralateral (control) striata showed a dramatic increase in kynurenic acid, equivalent to that seen in previous experiments. The inhibition of striatal ECF kynurenic acid response by AOAA was dose dependent. Infusion of control artificial ECF into the contralateral striata resulted in 29.56±10.01 fold increase in kynurenic acid while the striata receiving 1.0 and 2.0 mM AOAA resulted in only a 6.29±1.79 fold and 4.75±0.40 fold increase respectively.

Figure 6A:
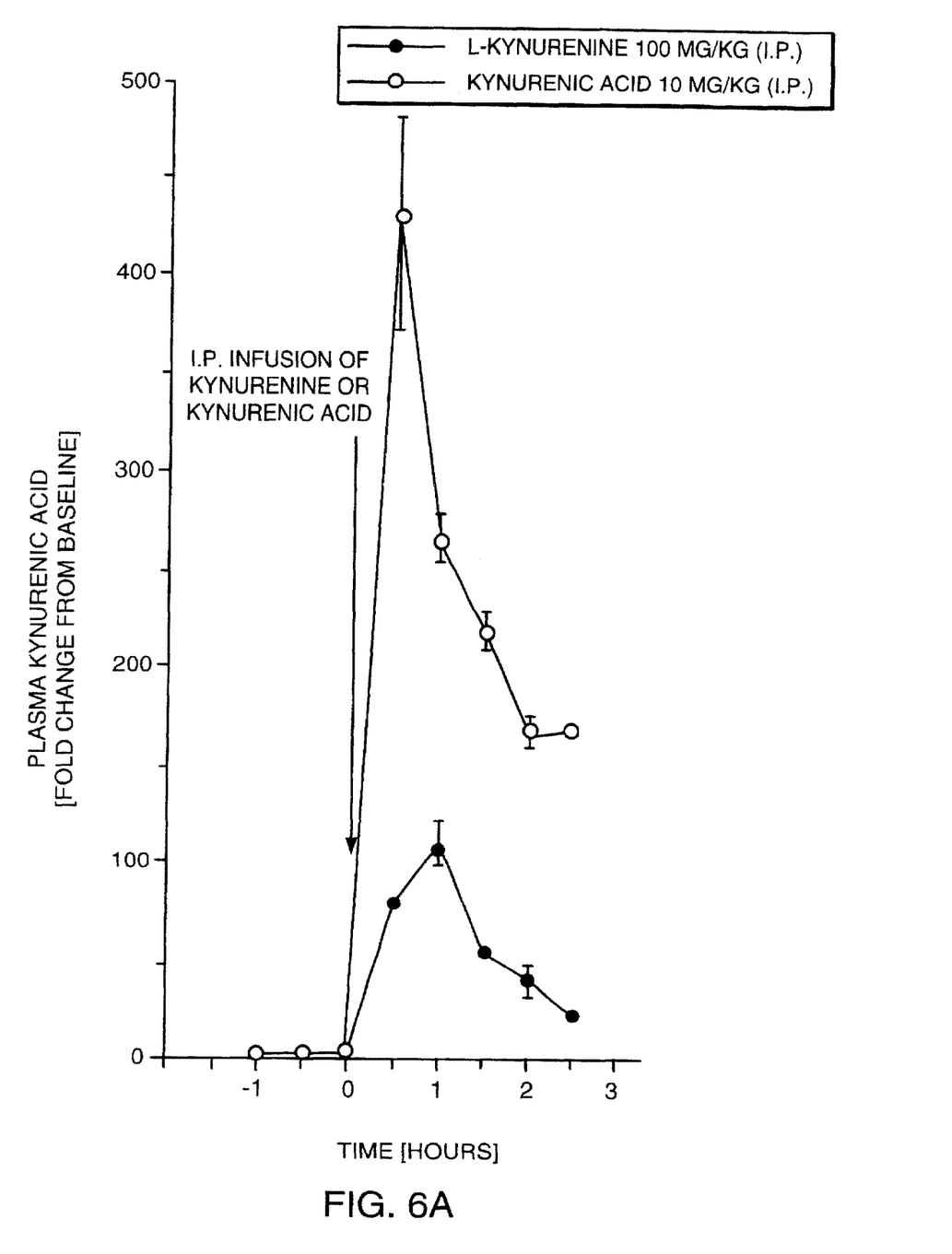
FIG. 6 shows plasma and striatal extracellular concentrations of kynurenic acid after peripheral injections (i.p.) of L-kynurenine or kynurenic acid. A: Plasma concentrations of kynurenic acid after L-kynurenine (100 mg kg$^{-1}$) or kynurenic acid (10 mg kg$^{-1}$) peripheral infusions. Plasma kynurenic acid concentrations after kynurenic acid acid infusions were significantly larger (p<0.01) than changes after injection of L-kynurenine by ANOVA. B: Striatal ECF concentrations of kynurenic acid after L-kynurenine (100 mg kg$^{31}$ $^{1}$) or kynurenic acid (10 mg kg$^{31}$ $^{1}$) peripheral injections.
Figure 6B:
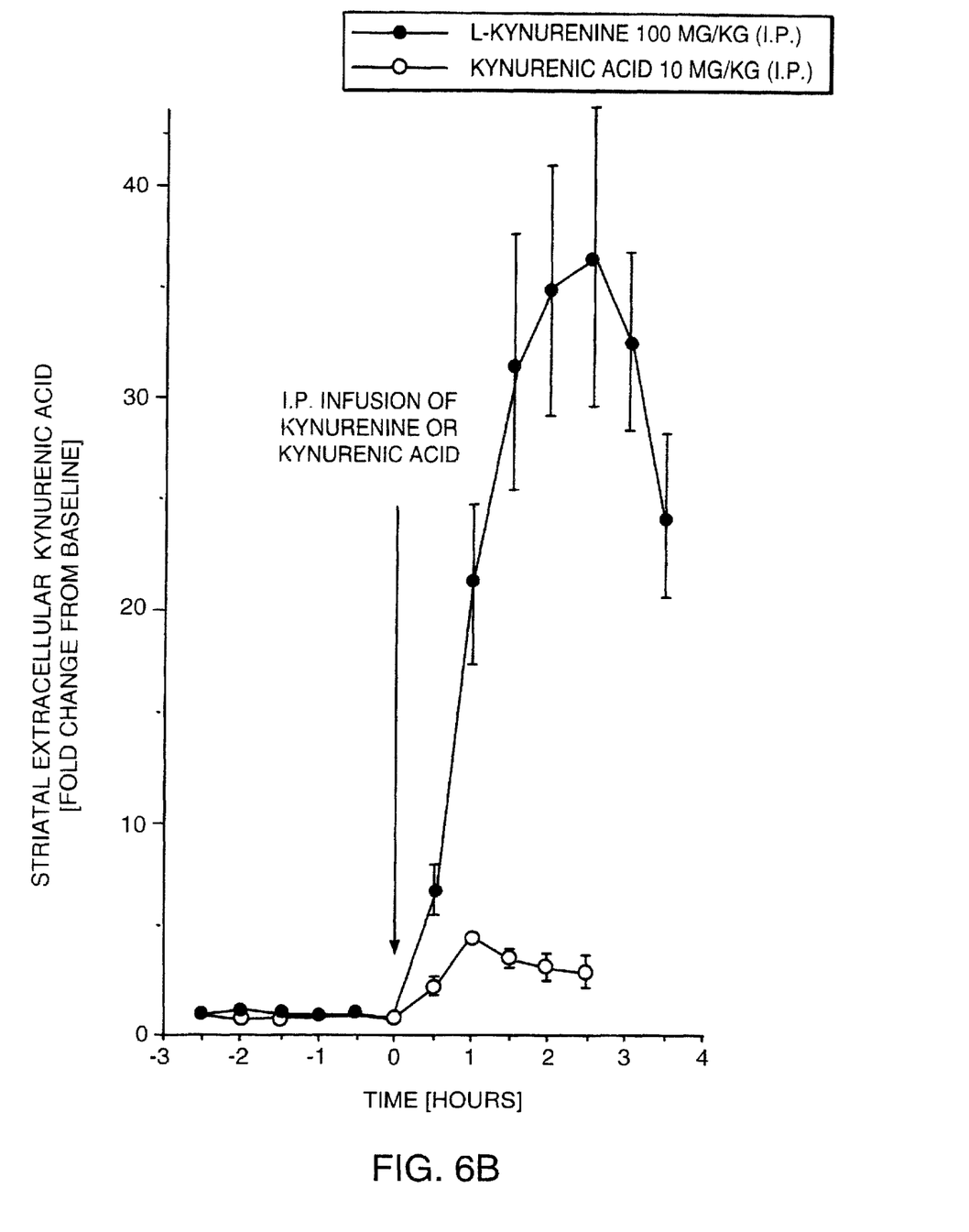

The peripheral formation of kynurenic acid from L-kynurenine was also examined. In 6 rats, basal levels of kynurenic acid in plasma were 137.9±25.5 nM. As shown in FIG. 6, at the highest dose of L-kynurenine (100 mg kg$^{-1}$), plasma levels of kynurenic acid increased 108.7±11.7 fold (peaking at 1 hour) while striatal ECF levels of kynurenic acid increase 37.1±7.0 fold (peaking at 2.5 hours). From data obtained in other preliminary experiments we estimated that a dose of 10 mg kg$^{-1}$ of kynurenic acid administered peripherally would cause increase in plasma kynurenic acid of equal or greater magnitude than seen with L-kynurenine (100 mg kg$^{-1}$). As shown in FIG. 6A, intraperitoneal administration of kynurenic acid (10 mg kg$^{-1}$) caused plasma levels of kynurenic acid to increase 430.7±52.8 fold (peaking at 30 minutes). Simultaneous striatal dialysis measurements showed that under these conditions, the striatal ECF concentrations of kynurenic acid increased only 4.6±0.4 fold (see FIG. 6B). The peripheral infusion of kynurenic acid (10 mg kg$^{-1}$) therefore caused four fold larger increases in plasma kynurenic acid than did L-kynurenine (100 mg kg$^{-1}$), but striatal ECF levels of kynurenic acid were increased 10 fold more by peripheral infusions of L-kynurenine than by peripheral infusions of kynurenic acid.

EXAMPLE 3
Effects of Kynurenine Loading on Brain Concentrations of Kynurenine and Kynurenic Acid In an initial experiment 200 gm male CD rats treated with kynurenine 200 mg/Kg i.p. and sacrificed at 1 hour. Controls received saline. At the time of sacrifice animals were either perfused transcardially with saline to remove blood within the intracranial or vessels, or not perfused. Kynurenine and kynurenic acid were measured as previously described. The striatum and cerebral cortex were dissected. Kynurenine increased in the striatum from 44±0.06 ng/mg protein to 32.7±9.5 ng/mg protein in non-perfused animal, and 41.1±7.4 ng/mg protein in the perfused animals. In the cerebral cortex kynurenine increased from 0.75±0.13 ng/mg protein to 27.6±7.0 ng/mg protein in non-perfused and 30.3±3.9 ng/mg protein in perfused animals. Kynurenine acid changes paralleled those of kynurenine. We conclude that the blood content of kynurenine and kynurenic acid does not appreciably affect measured brain levels.

EXAMPLE 4
Dose-Repsonse of Kynurenine on Brain Kynurenic Acid Concentrations Male CD rats weighing 175–200 gm were treated with kynurenine sulfate i.p. at doses of 150 mg/kg, 300 mg/kg, 450 mg/kg, 600 mg/kg and 750 mg/kg. Eight animals were examined in each group. At 2 hours animals were sacrificed and the brains were promptly removed and chilled on ice. The striatum and cerebral cortex were dissected, and a blood sample was collected into EDTA tubes. Kynurenine loading resulted in dose-responsive increases in both kynurenine and kynurenic acid in the plasma, striatum and cerebral cortex. The maximal increase in kynurenic acid was 4-fold and increases appeared to be leading off at the highest does levels.

Figure 7:
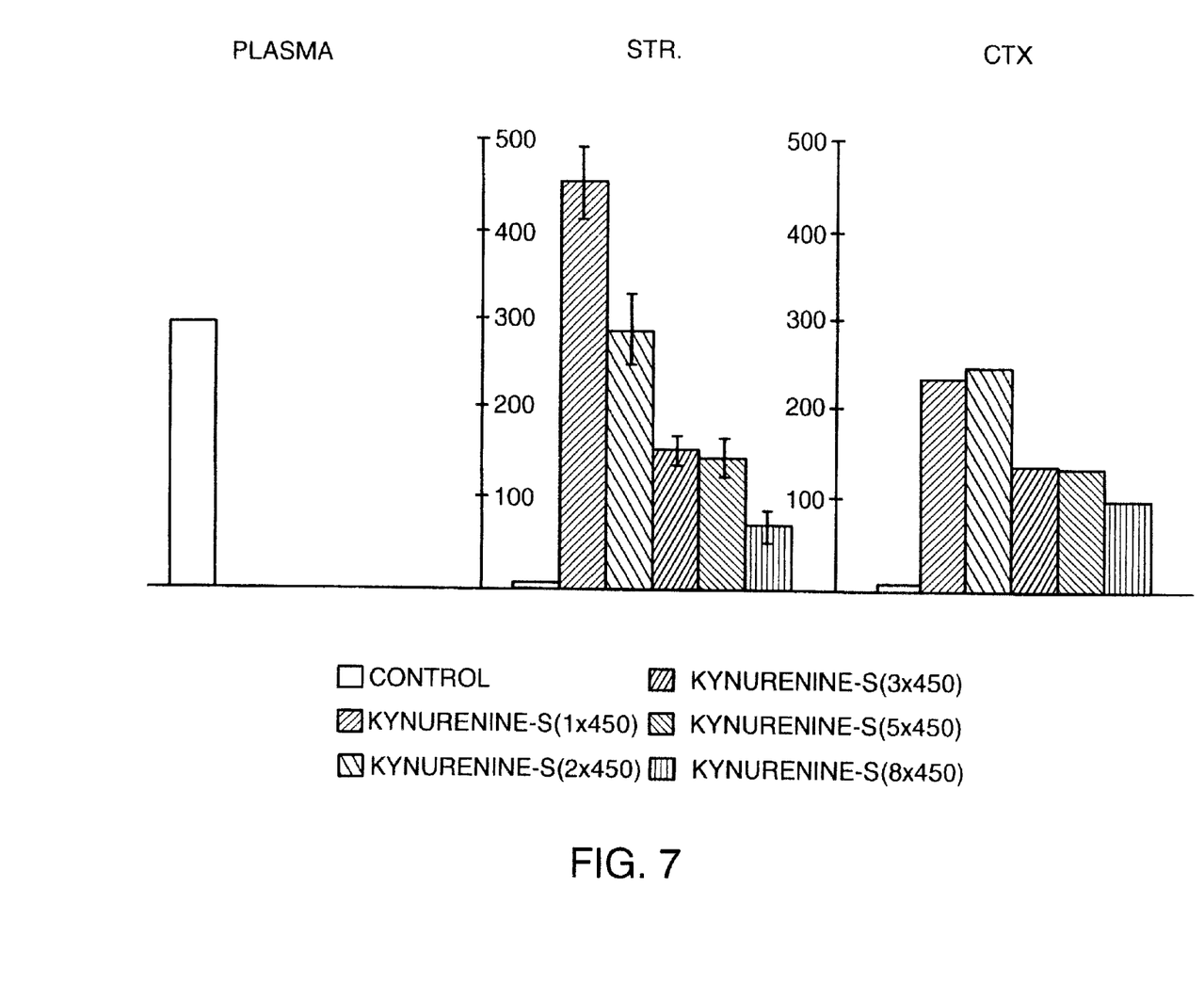
FIG. 7 shows the time course of kynurenine in the plasma, striatum and cerebral cortex after kynurenine sulfate injection.
Figure 8:
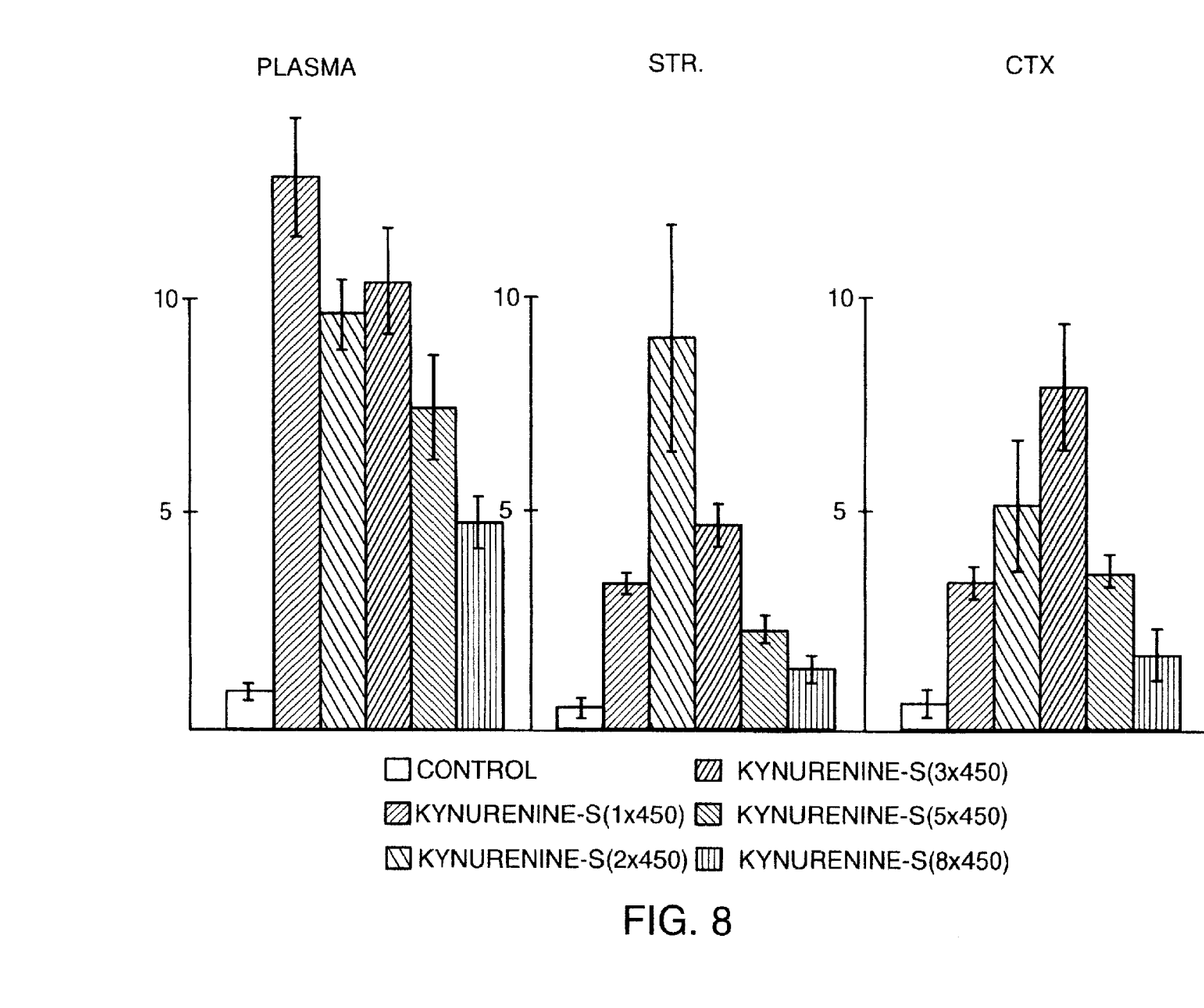
FIG. 8 shows the time course of kynurenic acid in the plasma stratium and cerebral cortex after kynurenine sulfate injection.

EXAMPLE 5
Time Course of Kynurenic Acid Concentrations Following Repeated Doses of Kynurenine Male CD rats weighing 175–200 gm were treated with kynurenine sulfate 450 mg/kg i.p. daily, and sacrificed two hours after the injection. The striatum, cerebral cortex and plasma were measured for concentrations of both kynurenine and kynurenic acid as above. Results are shown in FIGS. 7 and 8. Repeated kynurenine loading lead to marked increases in both brain and plasma kynurenine and kynurenic acid. Concentrations however down regulated over time, so that at one week concentrations remained between 8 and 16 fold above baseline levels. We have also examined the time course of disappearance of kynurenic acid after a single i.p. dose. At 2 hours concentrations were markedly elevated, but they returned almost to baseline by 24 hours, showing that kynurenic acid is rapidly excreted from the brain. We have also examined the effects of kynurenine in combination with probenecid, which inhibits excretion of kynurenic acid from the brain. This led to a marked potentiation of the level of brain kynurenic acid from a given dose of kynurenine.

EXAMPLE 6
Neuroprotective Effects of Kynurenine Loading in Ischemia
Neonatal Model Pregnant rats were purchased from Charles River. One week after delivery neonatal animals were anesthetized with methoxyflurane and underwent a unilateral ligation of the carotid artery. The animals were allowed to recover for 1 hour in an incubator. They were then treated with either saline of kynurenine at a dose of 600 mg/kg i.p. One hour later they were placed in a temperature (36.5° C.) controlled chamber, and exposed to 8% oxygen for 1½ hours. Nine control and 9 treated animals were sacrificed 4 days after exposure and stained with tetrazolium to assess infarct size. In addition, the size of the ischemic hemisphere was measured as compared to the contralateral hemisphere as a marker for diffuse ischemic damage. The volume of the infarct in the control group was significantly reduced (p<.01) from 20.45±9.03 to 0.46±0.46 The controls showed a significant reduction in the volume of the ipsilateral hemisphere of 251.8±11.8 from 300.4±11.7 on the contralateral side, while the kynurenic acid treated animals showed no significant differences in brain volumes (273.9±12.6 versus 276.3±11.9)

Adult Model

Adult 200–250 g male Fisher 344 rats were examined in a model of tandem common carotid artery and middle cerebral artery occulsion. Animals were pretreated with either saline or kynurenine 600 mg/kg i.p. 1 hour before occlusion of the middle cerebral artery. Arterial blood gases, pH, mean arterial blood pressure, blood glucose and body temperature showed no significant differences between 2 groups. Eight animals were examined in each group. After 4 days survival the animals were sacrificed and the volume of the infarct was determined using tetrazolium staining. The infarct volume in the treated animals was significantly reduced from that in the controls (128.0±5.7 versus 160.8±10.4, p<.05)

EXAMPLE 7

Anti-epileptic Effects and Anti-seizure Induced Mortality Effects

Male Swiss-Webster rats were treated with either saline or various doses of kynurenine i.p. 2 hours prior to treatment with pentylenetetrazole 90 mg/kg. The animals were then examined for both the duration to onset of grand-mal seizures, and to death. In the controls the duration to seizures was 62.3±5.2 sec, and time to death 17.5±3.1 min (n=16), at a dose of 450 mg/kg the onset was 96.7±11.4 sec and the time to death 23.9±2.3 min (n=24), and at 900 mg/kg the onset was 167±32 sec and time to death 18.9±3.1 min (n=10).

The effects of kynurenine pretreatment versus N-methyl-D, L-aspartate (NMDLA) induced seizures were also examined in Swiss-Webster mice. Animals received either saline, kynurenine, or diazepam 2 hour prior to 500 mg/kg of NMDLA. Animals were then assessed for time to excitation, time to seizures, and time to death. Kynurenine showed dose-dependent protective effects which were comparable to diazepam at the highest dose levels. Controls (saline) showed excitation at 4.1±0.4 min, seizures at 5.5±0.4 min and death at 7.4±0.4 min (n=22). Diazepam 2 mg/kg increased the time to excitation to 7.5±1.3 min, that to seizures to 10.2±1.3 min and death to 19.1±2.6 min (n=7). Kynurenine at 150 mg/kg resulted in time to excitation= 3.7±0.7 min, time to seizures 5.5±0.8 min, time to death 9.0±1.5 min (n=6). At a dose of 450 mg/kg kynurenine resulted in a time to excitation of 5.5±0.9 min, time to seizures 6.9±1.1 min and time to death 9.8±1.5 min (n=14). At a dose of kynurenine of 900 mg/kg the time to excitation was 7.2±1.3 min, time to seizures 9.9±1.3 min, and time to death 14.6±1.6 min (n=13).

To determine whether probenecid can potentiate the effects of kynurenic acid animals were pretreated with saline, probenecid 200 mg/kg kynurenine 450 mg/kg or probenecid 200 mg/kg with Kynurenine 450 mg/kg. Two hours later they received pentylenetetrazol 90 mg/kg. In the control group all animals developed seizures and 3/6 survived. With probenecid alone 1 animal developed seizures and 5/6 survived. With kynurenine alone 1 animal developed seizures and 5/6 survived. With combined probenecid and kynurenine all animals survived, and none developed seizures.

Equivalents

Those skilled in the art will recognize, or be able to ascertain, using no more than routine experimentation, many equivalents to the specific embodiments of the invention described herein. Such equivalents are intended to be encompassed by the following claims.

What is claimed is:

1. A method for treating kynurenic acid treatable neurological disease in an individual comprising administering a metabolic precursor of kynurenic acid to said individual, wherein said metabolic precursor is metabolized to said kynurenic acid in the brain of said individual, thereby ameliorating said kynurenic acid treatable neurological disease.

2. The method of claim 1 wherein said metabolic precursor is selected from the group consisting of kynurenine, kynurenine analogues that are metabolizable to kynurenic acid analogues and tryptophan.

3. The method of claim 2 wherein said administration comprises peripheral loading.

4. A method for treating kynurenic acid treatable neurological disease in an individual comprising administering a substance that causes the increased uptake in the brain of said individual of a metabolic precursor of kynurenic acid, thereby ameliorating said kynurenic acid treatable neurological disease.

5. The method of claim 4 wherein said metabolic precursor is kynurenine.

6. A method for treating kynurenic acid treatable neurological disease in an individual comprising administering a substance that increases the amount or activity of kynurenine aminotransferase in the brain of said individual, thereby ameliorating said kynurenic acid treatable neurological disease.

7. A method of increasing kynurenine levels in brain tissue in an individual, comprising administering to the individual kynurenine or tryptophan in a therapeutically effective amount.

8. The method of claim 7 further comprising administering an inhibitor of kynureninase or an inhibitor of 3-hydroxyanthranilic acid oxidase.

* * * * *

UNITED STATES PATENT AND TRADEMARK OFFICE
CERTIFICATE OF CORRECTION

PATENT NO. : 6,265,442 B1
DATED : July 24, 2001
INVENTOR(S) : M. Flint Beal et al.

It is certified that error appears in the above-identified patent and that said Letters Patent is hereby corrected as shown below:

Title page,
Item [75], Inventors, should read -- M. Flint Beal, Boston, MA; Andrew Frecse, Haverford, PA; Matthew J. During, Rowayton, CT; Kenton J. Swartz, Somerville, MA --.

Signed and Sealed this

Sixth Day of December, 2005

JON W. DUDAS
*Director of the United States Patent and Trademark Office*